United States Patent [19]
Haskill et al.

[11] Patent Number: 5,858,688
[45] Date of Patent: Jan. 12, 1999

[54] GRO GENES, PROTEINS, AND USES THEREOF

[75] Inventors: John Stephen Haskill, Chapel Hill, N.C.; Peter Ralph, Orinda, Calif.; Danute E. Nitecki, Berkeley, Calif.; George Martin, Berkeley, Calif.

[73] Assignees: Chiron Corporation, Emeryville, Calif.; University of North Carolina at Chapel Hill, Chapel Hill, N.C.

[21] Appl. No.: 474,362

[22] Filed: Jun. 7, 1995

Related U.S. Application Data

[62] Division of Ser. No. 190,249, Jan. 31, 1994, which is a continuation of Ser. No. 590,223, Sep. 28, 1990, abandoned.

[51] Int. Cl.$^6$ .......................... G01N 33/53; G01N 33/48
[52] U.S. Cl. ......................... 435/7.21; 435/7.24; 435/29; 436/501; 436/63
[58] Field of Search ................................. 435/7.21, 7.24, 435/29; 436/501

[56] References Cited

U.S. PATENT DOCUMENTS

| 4,603,106 | 7/1986 | Cerami. |
| 5,154,921 | 10/1992 | Sager et al. . |

FOREIGN PATENT DOCUMENTS

| 0 212 489 | 3/1987 | European Pat. Off. . |
| 0535 150 B | 4/1993 | European Pat. Off. . |
| WO 90/02762 | 3/1990 | WIPO . |
| WO 92/00327 | 1/1992 | WIPO . |

OTHER PUBLICATIONS

Anisowicz et al., "Constitutive Overexpression of a Growth–Related Gene in Transformed Chinese Hamster and Human Cells", *Proc. Natl. Acad. Sci. USA* (Oct., 1987) 84:7188.

Baker et al., "Nucleotide Sequence of the Human Melonoma Growth Stimulatory Activity (MGSA) Gene", *Nucleic Acids Research* (Sep., 1990) 18(21):6453.

Brown et al., "A Family of Small Inducible Proteins Secreted by Leukocytes are Members of a New Superfamily that Includes Leukocytes and Fiberglass–Derived Inflammatory Agents, Growth Factors, and Indicators of Various Activation Processes", *J. Immunol.* (Jan., 1989) 142:679.

Broxmeyer et al., "Myeolopoietic Enchancing Effects of Murine Macrophage Inflammatory Proteins 1 and 2 on Colony Formation in Vitro by Murine and Human Bone Marrow Granulocyte/Macrophage Progenitor Cells", *J. Exp. Med.* (Nov., 1989) 170:1583.

Cochran et al., "Molecular Cloning of Gene Sequences Regulated by Platelet–Derived Growth Factor", *Cell* (Jul., 1983) 33:939.

Davatelis et al., "Cloning and Characterization of a cDNA for Murine Macrophage Inflammatory Protein (MIP), a Novel Monokine with Inflammatory and Chemokinetic Properties", *J. Exp. Med.* (Jun., 1988) 167:1939.

Furuta et al., "Production and Characterization of Recombinant Human Neutropil Chemotactic Factor", *J. Biochem.* (Feb., 1989) 106:436.

Gimbrone et al., "Endothelial Interleukin–8: A Novel Inhibitor of Leukocyte–Endothelial Interactions", *Science* (Dec., 1989) 246:1601.

Graham et al., "Identification and Characterization of an Inhibitor of Haemopoietic Stem Cell Proliferaton", *Nature* (Mar., 1990) 344:442.

Haskill et al., "Identification of Three Related Human GRO Genes Encoding Cytokine Functions", *Proc. Natl. Acad. Sci. USA* (Oct., 1990) 87:7732.

Kwon et al., "cDNA Sequences of Two Inducible T–Cell Genes", *Proc. Natl. Acad. Sci. USA* (Mar., 1989) 86:1963.

Lindley et al., "Synthesis and Expression in *Escherichia coli* of the Gene Encoding Monocyte–Derived Neutrophil–Activating Factor: Biological Equivalence Between Natural and Recombinant Neutrophil–Activating Factor", *Proc. Natl. Acad. Sci. USA* (Dec., 1988) 85:9199.

Lipes et al., "Identification Cloning and Characterization of an Immune Activation Gene", *Proc. Natl. Acad. Sci. USA* (Dec., 1988) 85:9704.

Luster et al., "Biochemical Characterization of a γ Interferon–Inducible Cytokine (IP–10)", *J. Exp. Med.* (Oct., 1987) 166:1084.

Maione et al., "Inhibition of Angiogenesis by Recombinant Human Platelet Factor–4 and Related Peptides", *Science* (Jan., 1990) 247:77.

Miller et al., "A Novel Polypeptide Secreted by Activated Human T. Lymphocytes", *J. Immunol.* (Nov., 1989) 143:2097.

Mullenbach et al., "Chemical Synthesis and Expression in Yeast of a Gene Encoding Connective Tissue Activating Peptide–III", *J. Biol. Chem.* (Jan., 1986) 261:719.

Obaru et al., "A cDNA Clone Used to Study mRNA Inducible in Human Tonsillar Lymphocytes by a Tumor Promoter", *J. Biochem.* (Oct., 1986) 99:885.

Oquendo et al., "The Platelet–Derived Growth Factor–Inducible KC Gene Encodes a Secretory Protein Related to Platelet Alpha–Granule Proteins", *J. Biol. Chem.* (Mar., 1989) 264:4133.

(List continued on next page.)

*Primary Examiner*—Toni R. Scheiner
*Attorney, Agent, or Firm*—Ling-Fong Chung; Kenneth D. Sibley; Robert P. Blackburn

[57] ABSTRACT

Two novel cytokines which are involved in an inflammatory response (inflammatory cytokines) are disclosed. The inflammatory cytokines have been isolated from activated peripheral blood, preferably monocytes adhered to plastic; or peripheral blood leukocytes induced with calcium ionophore and mezerin. The two cytokines are Gro β and γ, and their cDNA and amino acid sequences are disclosed. The expression of the genes in various cells is presented. Assay and diagnostic utilities using the cytokines; recombinant materials and procedures; purification procedures; and monoclonal antibodies to the cytokines are also shown.

1 Claim, 4 Drawing Sheets

OTHER PUBLICATIONS

Richmond et al., "Molecular Characterization and Chromosomal Mapping of Melanoma Growth Stimulatory Activity, a Growth Factor Structurally Related to B–Thromboglobulin", *EMBO J.* (Mar., 1988) 7:2025.

Rollins et al., "Cloning and Expression of JE, A Gene Inducible by Platelet–Derived Growth Factor and Whose Product has Cytokine–Like Properties", *Proc. Natl. Acad. Sci. USA* (Jun., 1988) 85:3738.

Sager et al., "GRO as a Cytokine", *Mol. and Cellular Biol. Of Cytokines*, (1990) 327.

Sherry et al., "Resolution of the Two Components of Macrophage Inflammatory Protein 1, and Cloning and Characterization of One of Those Components, Macrophage Inflammatory Protein 1 beta", *J. Exp. Med.* (Dec., 1988) 168:2251.

Sporn et al., "Monocyte Adherence Results in Selective Induction of Novel Gene Sharing Homology ith Mediators of Inflammation and Tissue Repair", *J. Immunol.* (Jun., 1990) 144:4434.

Trask et al., "The GRO Gene as Growth Factor and Cytokine", *J. Cell Biochem Suppl O(14 part B)* (Jan., 1990) 5.

Wolpe et al., "Macrophages Secrete a Novel Heparin–Binding Protein with Inflammatory and Neutrophil Chemokinetic Properties", *J. Exp. Med.* (Feb., 1987) 167:570.

Wolpe et al., "Identification and Characterization of Macrophage Inflammatory Protein 2", *Proc. Natl. Acad. Sci. USA* (Jan., 1988) 86:612.

Yamamura et al., "Synthesis of a Novel Cytokine and its Gene (LD78) Expressions in Hematopoietic Fresh Tumor Cells and Cell Lines", *J. Clin. Invest.* (Dec., 1989) 84:1707.

Zipfel et al., "Mitogenic Activation of Human T Cells Induces Two Closely Related Genes which Share Structural Similarities with a New Family of Secreted Factors", *J. Immunol.* (Mar., 1989) 142:1582.

Tekamp–Olson, et al., *J. Exp. Med.*, vol. 172, pp. 911–919, 1990.

Lee, J.C., et al., *Agents Actions*, vol. 27, No. 3–4, pp. 277–279, 1989.

GRO GENES, PROTEINS, AND USES THEREOF

This application is a divisional of application Ser. No. 08/190,249, filed 31 Jan. 1994, which is a continuation of application Ser No. 07/590,223, filed 28 Sep. 1990, now abandoned.

FIELD OF THE INVENTION

This invention relates generally to the field of molecular biology/immunology and diagnostic uses therein.

BACKGROUND OF THE INVENTION

The present invention involves novel cytokines, in particular Gro genes and proteins, which were derived from the cDNAs of induced peripheral blood cells, for example monocytes. Therefore, the following discussion presents the background on cytokines, monocytes and the Gro genes and proteins.

A. Cytokines

Cytokines are small molecular weight proteins that have a broad range of cell regulatory activity both in vitro and in vivo. (For background information, see Balkwill, F. R., al., 1989, *Immun. Today,* 10: 299). Some cytokines possess growth factor activity. Examples of cytokines which can inhibit cell growth or directly kill cells are interferons (IFNs), tumor necrosis factor (TNF), lymphotoxin (LT), the interleukin 1s (IL-1s) and transforming growth factor β (TGF-β). Most cytokines act on B or T cells at some stage in their response. An example of the physiological effect of cytokines can be seen in the case of cytokines which regulate the inflammatory response by varying the T and B lymphocyte activation, chemotaxis, eicosanoid secretion and collagen production. Differential expression of these inflammatory mediators may influence the perpetuation of chronic inflammation and fibrotic manifestations.

B. Monocytes

Monocytes are directed to sites of infection by chemotactic factors released as a result of inflammation or infection (Sporn, S. A., et al., 1990, *J. of Immun.,* 144:4434–4441). The migration of monocytes into the tissue involves interaction with vascular endothelium and the subsequent migration of the monocytes through the underlying basement membrane, during which the monocytes come into close contact with extracellular matrix components and connective tissue cells (Harlan, J. M, 1985, *Blood,* 65:513; Wilkinson, P. C., et al., 1979, *Curr. Top Pathol.,* 68:47).

Thorens, B., et al., 1987, *Cell,* 48:671 reported that adherence might be important in transcriptional expression of macrophage mediators of inflammation and that adherence to different matrices could result in preferential gene induction. Further, there is evidence for participation of cell adhesion molecules in developmental interaction between epithelial and mesenchymal cells influencing cell differentiation (Sanders, E. J., 1988, *Biochem. Cell Biol.,* 66:530). It has also been shown that within 30 minutes of monocyte adherence to plastic, a complex set of regulatory events is initiated as defined by rapid changes of mRNA levels of several proto-oncogenes and inflammatory mediators (Haskill, S., et al., 1988, *J. of Immunol.,* 140:1690). IL-1β, TNF-α and c-fos are rapidly elevated, whereas CSF-1 steady state mRNA levels increase by 90 minutes. In contrast, expression of c-fms and lysozyme is rapidly down-regulated. These genes are modulated by adherence to different biologically relevant substrates (Eierman, D. F., 1989, *J. of Immunol.,* 142:1970–1970).

Although high steady state mRNA levels of important mediators of inflammation are rapidly induced by adherence, adherence by itself is insufficient to cause efficient translation and secretion of IL-1β, TNF-α, or CSF-1 (Haskill, S., et al., supra). Activation by a second signal, such as bacterial endotoxin, is required for the secretion of all three gene products. Thus, it is clear that signals derived from the act of adherence are likely to play a significant role in the activation and differentiation of monocytes allowing them to respond to infection and to influence the local tissue environment (Sporn, S. A, supra). Recent studies indicate that adherence leads to a general activation of numerous genes involved in the early defense response and whose expression may be regulated by selective tissue/extracellular matrix interactions. Id.

C. Gro Genes/Proteins

Adherence of monocytes results in the rapid induction of high levels of mostly transient mRNAs for various novel inflammatory mediator genes (Sporn, S. A., et al., supra). One of these novel clones, Gro α, had a predicted amino acid sequence similar to that reported for the original Gro gene product Mapping studies of Gro (Anisowicz, A., et al., 1988, *PNAS (USA),* 85:9645–9649 and Richmond, A., et al., 1988, *EMBO J.,* 7:2025–2033) identified a unique Gro site at chromosome 4q21. The Gro gene belongs to a gene superfamily which encodes a set of related cytokines that includes NAP-1/IL-8 (Matsushima, K., et al., 1988, *J. Exp. Med.,* 167:1883–1893; Schmid, J., et al., 1987, *J. of Immunol.,* 139:250–256; Peveru, P., et al., 1988, *J. Exp. Med.,* 167:1547–1559), and platelet basic protein (PBP). PBP is the precursor of connective tissue activating protein III (CTAP III), β-thromboglobulin (Castor, C. W., et al., 1983, *PNAS (USA),* 80:765–769), platelet factor 4 (PF4) (Deuel, T. F, et al., 1977, *PNAS (USA),* 74:2256–2258), γ-interferon-inducible peptide (γIP-10) (Luster, A. D., et al., 1985, *Nature (London),* 315:672–676), and macrophage inflammatory protein 2 (MIP-2) (Wolpe, S. D., et al., 1989, *PNAS (USA),* 86:612–616).

Gro was initially identified by its constitutive over-expression in spontaneously transformed Chinese hamster fibroblasts (Anisowicz, A., et al., 1987, *PNAS (USA),* 84:7188–7192). A related gene was identified in v-src transformed chicken cells (Sugano, S., et al., 1987, *Cell,* 49:321–328; Bedard, P. A., et al., 1987, *PNAS (USA),* 84:6715–6719). In expression studies with normal fibroblasts, Gro showed early response kinetics similar to c-fos, leading to the name Gro (growth regulated) (Anisowicz, A., et al., 1987, supra). Later, a protein with melanoma stimulating activity (MGSA) (Richmond, A., et al., supra) was shown to be encoded by Gro, and sequence similarity was reported with the murine early response gene KC (Oquendo, P., et al., 1989, *J. Biol. Chem.,* 264:4133–4137).

Preliminary studies showed that the Gro α gene was expressed in active ulcerative colitis disease, but not in the inactive tissue. (Isaacs, K., et al., "Profiles of cytokine activation in inflammatory bowel disease tissue: measurement of cDNA amplification", American Gastroenterological Assoc. & American Assoc. for the Study of Liver Diseases, May 13–16, 1990, Texas (Abstract)). On the other hand, disparity in expression of the Gro α gene was less in the case of active versus inactive tissues from Crohn's disease. The expression of the Gro α gene in active intestinal inflammation suggests a role of these cytokines in the pathogenesis of inflammatory bowel disease.

A cDNA designated MAD-2 was shown at a 1988 RES Conference. (Sporn, S. et al., "Isolation of Adherence Specific cDNA Clones from a Monocyte cDNA Library" Society for Leukocyte Biology (RES), Washington, D.C., Oct. 27–30, 1988; and in Sporn, S. A. et al. *J. of Immunol,* 1990, 144:4434.) MAD-2 was isolated by differential hybridization from a cDNA library which was prepared in the bacterial expression vector γgt10 by using total RNA from human blood monocytes adhered to plastic for 30 minutes at 37° C. Sporn, S. A. et al., *J. of Immunol,* 1990, supra. MAD-2 and human Gro were believed to be separate gene products based on Southern blots analysis and differences in the amino acid sequences in the carboxyl-terminus amino acids. Id. at 4440. At the Cytokine Workshop of Dec. 13, 1989, Hilton Head, Ga., Ruth Sager presented the amino acid sequences of both Gro β and γ.

Recently, two cDNAs for the human homologs of murine MIP-2 had been cloned from a library prepared from phorbol myristate acetate (PMA)—treated and lipopolysaccharide (LPS)—stimulated U937 cells Tekamp-Olson, P. et al., 1990, *J. Exp. Med.,* 172:911. These cDNAs, designated MIP-2γ and MIP-2β are closely homologous to the cDNAs disclosed in the pending patent application.

SUMMARY OF THE INVENTION

One aspect of the invention presents two novel inflammatory cytokine genes, Gro β and γ, that have been found in peripheral blood cell cDNA libraries.

Another aspect of the invention presents the cDNA and amino acid sequences of Gro β and γ and methods for obtaining them.

Another aspect of the invention presents a description of the expression of Gro β and γ genes in various cells.

Another aspect of the invention presents the uses of Gro β and γ for detecting agents which cause inflammation (hereinafter referred to as inflammatory agents), or agents which prevent or reduce inflammation (hereinafter referred to as anti-inflammatory agents).

Another aspect of the invention presents the use of Gro γ or β for diagnosing cancer, preferably human colonic cancer in the case of Gro γ.

Another aspect of the invention presents recombinant Gro β and γ and procedures for obtaining them.

Another aspect of the invention presents monoclonal antibodies against Gro β and γ.

Another aspect of the invention presents methods for purifying Gro β and γ proteins.

BRIEF DESCRIPTION OF THE DRAWINGS

FIGS. 1(*a*) and 1(*b*) show the cDNA sequences and predicted translation sequences of the open reading frames for Gro β and Gro γ compared with Gro α, noting positions of amino acid differences. Probes used for Southern DNA transfer and primers used for polymerase chain reaction (PCR) analysis of the RNAs are underlined. Bold typed regions indicate the positions of the ATTTA motif, and conserved regions between the 3 human Gro isolates are boxed (beginning at bp848 for Gro α) as well as a region common between human and hamster (bp930 Gro α).

DETAILED DESCRIPTION OF THE INVENTION

Figures 2A, 2B:
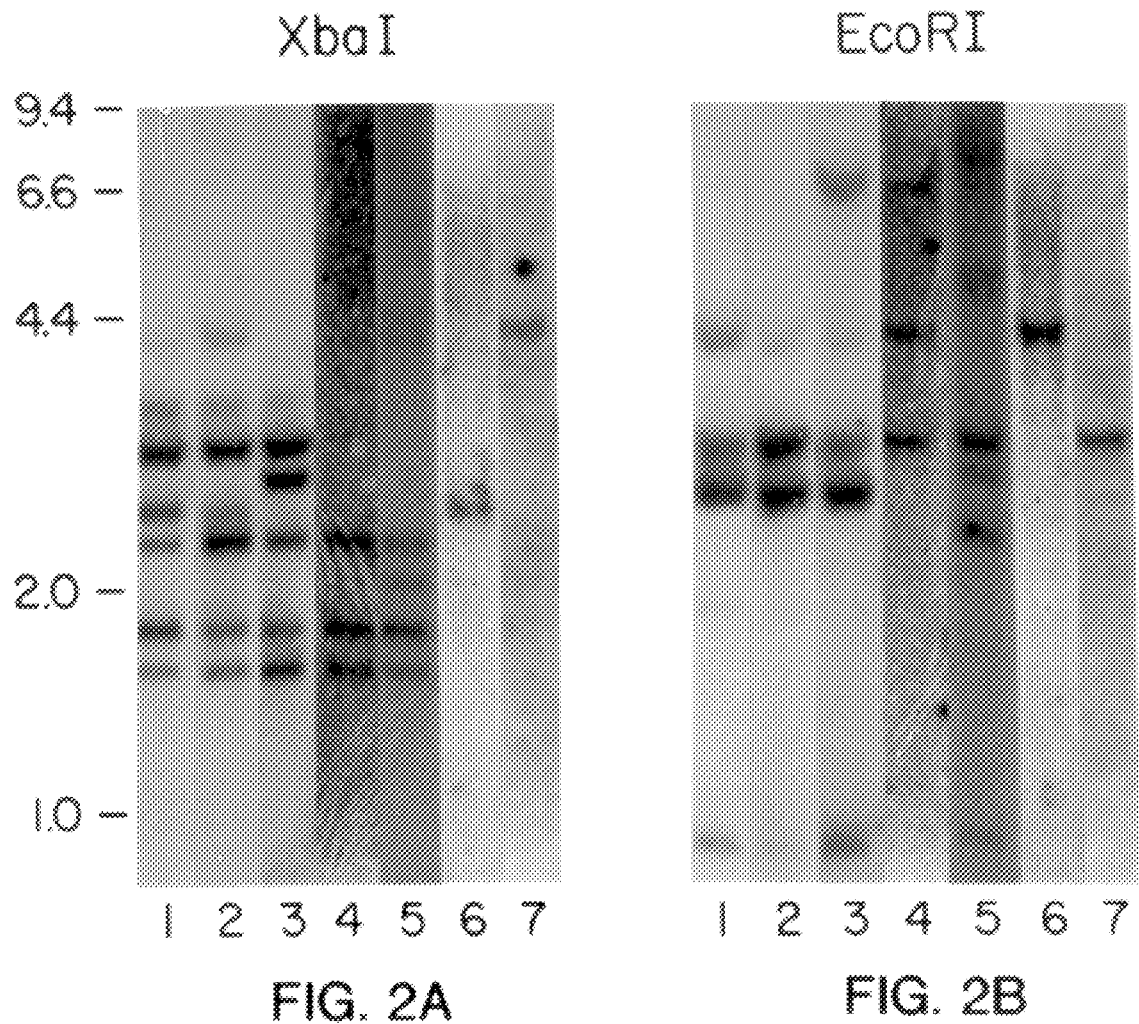
FIG. 2 shows the Southern transfer analysis which demonstrated the presence of three distinct Gro genes. Lanes 1–3, hybridization with the Gro α, β and γcDNA clones. Lanes 4–7, oligonucleotide hybridization to dehydrated agarose gels (Caput, D., et al., 1986, *PNAS (USA),* 83:1670–1674). Lane 4, oligonucleotide ML80; Lane 5, GM349; Lane 6, Gro α specific oligonucleotide (GM350); and Lane 7, Gro β specific oligonucleotide GM272.

The invention described herein draws on previously published work and pending patent applications. By way of example, such work consists of scientific papers, patents or pending patent applications. All of these publications and applications, cited previously or below are hereby incorporated by reference.

Although any similar or equivalent methods and materials may be employed in the practice or testing of the present invention, the preferred methods and materials are now described.

A. Definitions

Figure 1A:
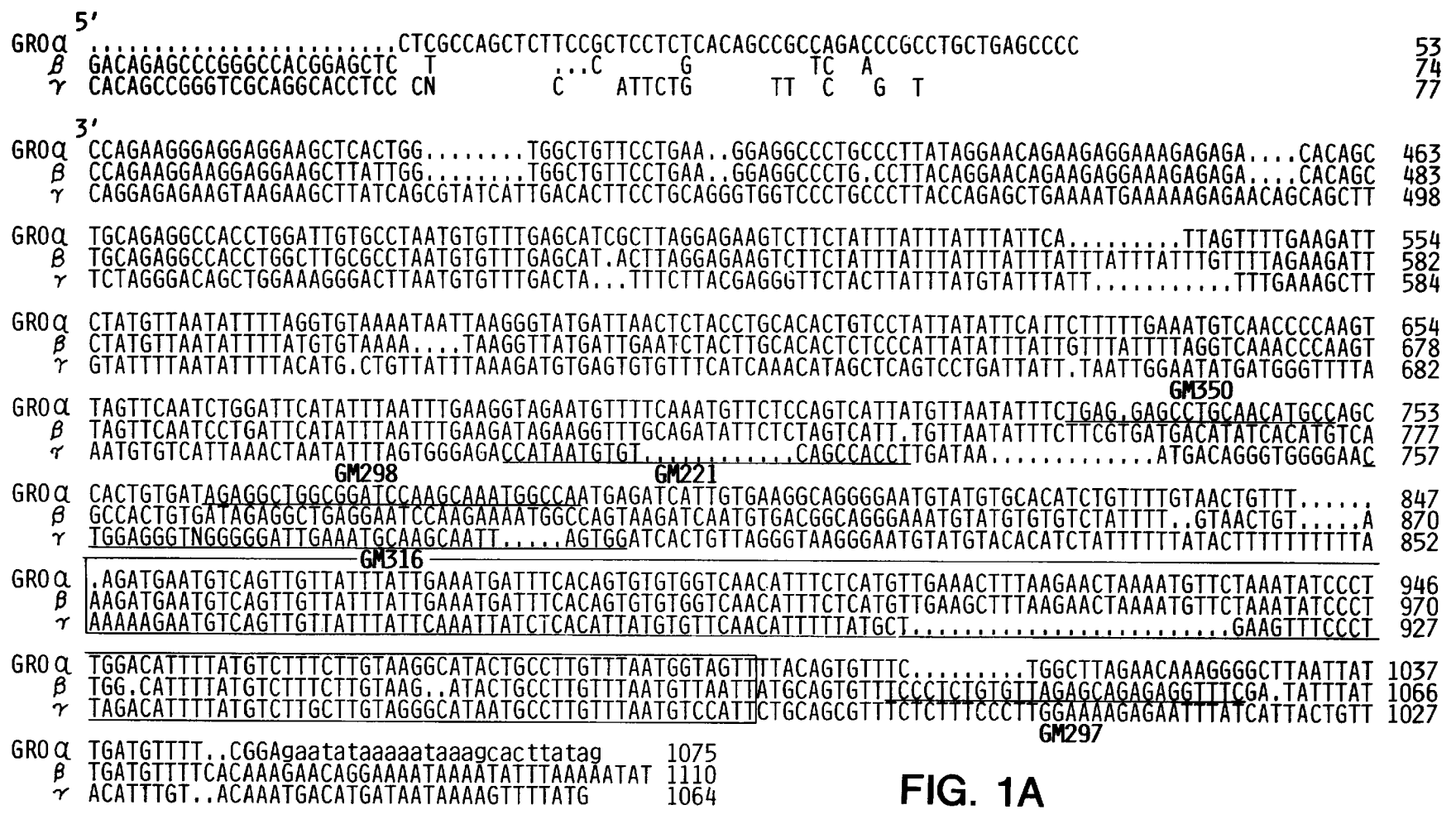

The term "Gro β" and "Gro γ" as used in relation to protein material throughout the present application and claims refer to protein materials having the amino acid sequences presented in FIG. 1(*b*) and their functional equivalents. Two amino acid sequences are functionally equivalent if they have substantially the same biological activities. Further included in the scope of "Gro β" and "Gro γ" are their propolypeptide and mature polypeptide forms. FIG. 1(*b*) shows the propolypeptides of Gro β and Gro γ which include their signal peptides or leader sequence. Cells secrete mature polypeptides which have their signal peptides removed. For therapeutic or diagnostic uses, the mature polypeptides are preferred over the propolypeptide. Further, different signal peptides can substitute for the naturally occurring ones. The mature polypeptide begins at about position 35 ($Ala_{35}$) for Gro β, and at about position 34 ($Ala_{34}$) for Gro γ.

Independent of their biological activities, two polypeptides are also considered functionally equivalent if they have similar sequences or display substantially equivalent sequences to the prolypeptide sequences of Gro β or Gro γ in FIG. 1(*b*) or their mature polypeptide sequences. Preferably, two polypeptides are functionally equivalent when at least about 88% of their amino acids match over a defined lengths of the mature polypeptides. For this calculation, there is a penalty of one wrong amino acid per mismatched or unmatched (deletion) residue.

Modified proteins are also within the contemplation of this patent application. These modifications may be deliberate, for example, such as modifications obtained through site-directed mutagenesis, or may be accidental, such as those obtained through mutations in the hosts.

Further, as is the case for all proteins, the precise chemical structure depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition. Additionally, the primary amino acid sequence may be augmented by derivatization using sugar moieties (glycosylation) or by other supplementary molecules such as lipids, phosphate, acetyl groups and the like, more commonly by conjugation with saccharides. The primary amino acid structure may also aggregate to form complexes, most frequently dimers. Certain aspects of such augmentation are accomplished through post-translational processing systems of the producing host; other such modifications may be introduced in vitro. In any event, such modifications are included in the definition so long as the activity of the protein is not destroyed. It is expected that such modifications may quantitatively or qualitatively affect the activity, either by enhancing or diminishing the activity of the protein in various assays.

Individual amino acid residues in the chain may also be modified by oxidation, reduction, or other derivatization, and the protein may be cleaved to obtain fragments which retain activity, Such alterations which do not destroy activity do not remove the protein sequence from the definition.

Modifications to the primary structure itself by deletion, addition, or alteration of the amino acids incorporated into the sequence during translation can be made without destroying the activity of the protein. Such substitutions or other alterations result in proteins having an amino acid sequence which falls within the definition of Gro β and γ proteins.

Among other things, the Gro proteins are involved in inflammatory response. The terms "inflammatory cytokine" is intended to include within its scope the Gro β and γ proteins specifically recited herein, as well as all their functional equivalents.

Similarly, the terms "Gro β" and "Gro γ" as used in relation to DNA sequences throughout the present application and claims refer to the DNA sequences presented in FIGS. 1(a) and (b) and their functional homologs. Also within the scope of this patent application are DNA sequences or fragments which encode protein or peptide having substantially the same biological activities as Gro β or γ. These DNA sequences or fragments are hereinafter called functional homologs.

Further, within the definition of functional homologs and independent of their biological activities, are DNA sequences which are substantially homologous to the DNA sequences of Gro β or γ presented in FIGS. 1(a) and (b) and the DNA sequences of their functional homologs. Two DNA sequences are "substantially homologous" when at least about 94% of the nucleotides match over the defined length of the DNA sequences, preferably the DNA sequences are without the leader sequence. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatas, et al., 1982, DNA Cloning: A Practical Approach, Vols. I & II, (Glover, D. N., ed. 1985); and Hanes, B. D., et al., 1985, Nucleic Acid Hybridization.

In Example 1 below, Gro β and γ were derived from the cDNA of activated or induced (the term "activation" and "induction" are used interchangeably) peripheral blood cells. The preferred cells are peripheral blood leukocytes and most preferably monocytes. The preferred activation method in the case of peripheral blood leukocytes are by means of mezerein and calcium ionophore. The preferred activation method in the case of monocytes is by means of adherence to extracellular matrixes or other substrates. The specific example shown was by adherence to plastic. However, other cell lines or other sources for the development of either the material from which the Gro β and Gro γ are thereafter isolated, or the Gro β and Gro γ themselves, are contemplated herein and the present invention is accordingly not limited. For example, within the contemplation of this patent application are cells which are activated or induced, for example by mitogens such as LPS or PMA or adherence to other extracellular matrixes or by viral infections, and thereby express Gro β or Gro γ. (An example of viral induction is seen in Dudding, L., et al., 1989, *J. Immunology*, 143:3343, "Human Cytomegalovirus Infection Stimulates Expression of Monocyte-Associated Mediator Genes".) Tumor cells which express Gro β or Gro γ are also within the contemplation of this patent application.

Alternate means, such as genetic replication which may be conducted according to principles of recombinant technology that are well known in the art are contemplated herein in accordance with the present invention.

Thus, Gro β and Gro γ nucleic acid sequences may be obtained by screening genomic or cDNA library from any cell. The DNA may also be obtained by synthesizing the DNA using commonly available techniques and DNA synthesizing apparatus. Synthesis may be advantageous because unique restriction sites may be introduced at the time of preparing the DNA, thereby facilitating the use of the genes in vectors containing restriction sites not otherwise present in the native source. Further, any desired site modification in the DNA may be introduced by synthesis, without requiring further modification of the DNA by mutagenesis.

An "antibody" is defined herein to include any immunoglobulin, including antibodies and antigen binding fragments thereof (e.g., Fab, F(ab)$_2$, Fv), which bind a specific epitope. The term encompasses, inter alia, polyclonal, monoclonal, single chain and chimeric antibodies, the last mentioned are described in further detail in U.S. Pat. Nos. 4,816,397 and 4,816,567.

B. Establishment of a cDNA Library

A full length cDNA sequence that encodes the inflammatory cytokine may be obtained using molecular biology techniques well known in the art, with the noted exceptions detailed below.

Several procedures are available for identifying the cytokine cDNA sequences. The preferred procedure is to generate a library using RNA isolated from peripheral blood cells, more preferably peripheral blood leukocytes and monocytes, but a library can be generated from virtually any source of biological material that expresses the inflammatory cytokine; indeed, cDNA libraries can even be purchased commercially. Monocytes and peripheral blood cells are the preferred starting materials because the adherence of monocytes to an appropriate surface, and the activation of the peripheral blood leukocytes by calcium ionophore and mezerein, induce the expression of the inflammatory cytokines.

An illustrative procedure for making a cDNA library containing the inflammatory cytokine sequences consists of isolating total cytoplasmic RNA from a suitable starting material, and further isolating messenger RNA therefrom. The latter can be further fractionated into Poly (A+) messenger RNA, which in turn may be fractionated further still into Poly (A+) messenger RNA fractions containing inflammatory cytokine messenger RNA. The messenger RNA can then be reverse transcribed and cloned into a suitable vector to form the cDNA library.

More specifically, the starting material (i.e., tissue, cells) is washed with phosphate buffered saline, and a non-ionic detergent, such as ethylene oxide is added in an amount to lyse the cellular, but not nuclear membranes, generally about 0.3%. Nuclei can then be removed by centrifugation at 1,000×g for 10 minutes. The post-nuclear supernatant is added to an equal volume of TE (10 mM Tris, 1 mM ethylenediaminetetraacetic acid (EDTA), pH 7.5) saturated phenol/chloroform (1:1) containing 0.5% sodium dodecyl sulfate (SDS) and 10 mM EDTA. The supernatant is re-extracted 4 times and phase separated by centrifugation at 2,000×g for 120 minutes. The RNA is precipitated by adjusting the samples to 0.25M NaCl, adding 2 volumes of 100% ethanol and storing at −20° C. The RNA is then pelleted at 5,000×g for 30 minutes, washed with 70% and 100% ethanol, and dried. This represents the total cytoplasmic RNA.

Alternatively, total cytoplasmic RNA may be isolated using the guanidine isothiocyanate-cesium chloride method as described by Chirgwin et al., 1979, *Biochem.*, 18: 5294.

Polyadenylated (Poly A+) messenger RNA (mRNA) can be obtained from the total cytoplasmic RNA by chromatography on oligo (dT) cellulose (J. Aviv et al., 1972, *PNAS*, 69:1408–1412). The RNA is dissolved in ETS (10 mM Tris, 1 mM EDTA, 0.5% SDS, pH 7.5) at a concentration of 2 mg/ml. This solution is heated to 65° C. for 5 minutes, then quickly chilled to 4° C. After bringing the RNA solution to room temperature, it is adjusted to 0.4M NaCl and slowly passed through an oligo (dT) cellulose column previously equilibrated with binding buffer (500 mM NaCl, 10 mM Tris, 1 mM EDTA, pH 7.5) The flow-through is passed over the column twice more, and the column washed with 10 volumes of binding buffer. Poly (A+) mRNA is eluted with aliquots of ETS, extracted once with TE-saturated phenol chloroform and precipitated by the addition of NaCl to 0.2M and 2 volumes of 100% ethanol. The RNA is reprecipitated twice, washed once in 70% and then 100% ethanol prior to drying. The poly (A+) mRNA can then be used to construct a cDNA library.

cDNA can be made from the enriched mRNA fraction using oligo (dT) priming of the poly A tails and avian myeloblastosis virus (AMV) reverse transcriptase employing the method of H. Okayama et al., 1983, *Mol. Cell Biol.* 3:280.

Other methods of preparing cDNA libraries are, of course, well known in the art. One, now classical, method uses oligo (dT) primer, reverse transcriptase, tailing of the double stranded cDNA with poly (dG) and annealing into a suitable vector, such as pBR322 or a derivative thereof, which has been cleaved at the desired restriction site and tailed with poly (dC). A detailed description of this alternate method is found, for example, in U.S. Ser. No. 564,224, filed Dec. 20, 1983, and assigned to the same assignee.

Using the partial amino acid sequence of Gro α (see FIGS. 1(a) and (b)), and known codon redundancies thereto, several DNA oligonucleotide probes may be synthesized and used to screen the cDNA library.

A preferred method by which a cDNA clone that encodes the inflammatory cytokines may be identified is to employ a cDNA library that is produced using RNA obtained from induced monocytes or peripheral blood cells, and to detect individual clones that differentially hybridize to cDNA probes produced using RNA from induced and uninduced monocytes or peripheral blood cells. Clones that preferentially hybridize to cDNA probes produced from induced but not uninduced monocyte or peripheral blood cell RNA will contain cDNAs that encode the inflammatory cytokines of the instant invention.

cDNA inserts may be sequenced using known techniques. The preferred technique is to subclone the inserts into an appropriate vector, an exemplary vector being pGEM blue (Promega Biotec. Madison, Wisconsin Corp.), and sequence the double stranded DNA using the dideoxy chain termination method described by Sanger et. al., 1977, *PNAS (USA)*, 74:5463. Sequencing is conveniently performed using commercially available kits, preferably the Sequenase sequencing kit produced by United States Biochemical Co. Cleveland, Ohio, and using suitable primers, such as T7 and SP6 obtainable from Promega Biotec. Madison, Wis., and sequence specific primers.

C. Immunological Procedures for Detecting the Inflammatory Cytokines

The presence of the inflammatory cytokine can be ascertained by a number of immunological procedures known in the art. Examples of useful procedures include: the "competitive" procedure described in U.S. Pat. Nos. 3,654,090 and 3,850,752; the "sandwich" procedure described in U.S. Pat. Nos. RE 31,006 and 4,016,043; and the "double antibody" or "capture" procedure. In the capture procedure, three antibodies are used: $Ab_1$, $Ab_2$, and $Ab_3$. The procedure may be represented by the following equation: $Ab_1+Cyt+Ab_2+*Ab_3=Ab_1Cyt\ Ab_2*Ab_3$. Cyt represents the inflammatory cytokine, and $*Ab_3$ represents labelled $Ab_3$. $Ab_1$ and $Ab_2$ recognize the inflammatory cytokine, whereas the labelled $*Ab_3$ recognizes $Ab_2$. $Ab_1$ is bound to a support. The presence of the inflammatory cytokine is detected by the resulting labelled complex of $Ab_1Cyt\ Ab_2*Ab_3$.

In each of the procedures, the inflammatory cytokine forms complexes with one or more antibody(ies) or binding partners and one member of the complex is labelled with a detectable label. The fact that a complex has formed and, if desired, the amount thereof, can be determined by known methods applicable to the detection of labels.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The inflammatory cytokine or its binding partner(s) can also be labelled with a radioactive element or with an enzyme. The radioactive label can be detected by any of the currently available counting procedures. The preferred isotope may be selected from $^{14}C$, $^{131}I$, $^{3}H$, $^{125}I$ and $^{33}S$.

Enzyme labels are likewise useful, and can be detected by any of the presently utilized colorimetric spectrophotometric, fluorospectrophotometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labelling material and methods.

The above procedures and their applications are all familiar to those skilled in the art and accordingly may be utilized within the scope of the present invention.

D. Recombinant Procedures

The following describe general recombinant procedures, which could be modified by those skilled in the art for obtaining recombinant Gro β and γ.

1. Suitable Hosts, Control Systems and Methods

In general terms, the production of a recombinant form of Gro β or γ typically involves the following:

First, a DNA encoding the mature protein (used here to include all muteins); the preprotein; or a fusion of the Gro β or γ protein to an additional sequence which does not destroy its activity or to additional sequence cleaved under controlled conditions (such as treatment with peptidase) to give an active protein, is obtained. If the sequence is uninterrupted by introns it is suitable for expression in any host. If there are introns, expression is obtainable in mammalian or other eucaryotic systems capable of processing them. This sequence should be in excisable and recoverable form. The excised or recovered coding sequence is then placed in operable linkage with suitable control sequences in a replicable expression vector. The vector is used to transform a suitable host and the transformed host cultured under favorable conditions to effect the production of the recombinant Gro β or γ.

Genomic or cDNA fragments are obtained and used directly in appropriate hosts. The constructions for expression vectors operable in a variety of hosts are made using appropriate replications and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, procaryotic, yeast, or mammalian cells are presently useful as hosts. Host systems which are capable of proper post-translational processing are preferred. Accordingly, although procaryotic hosts are in general the most efficient and convenient for the production of recombinant proteins, eucaryotic cells, and, in particular, mammalian cells are preferred for their processing capacity, for example, the ability to form the proper glycosylation patterns. In addition, there is more assurance that the native signal sequence will be recognized by the mammalian host cell, thus making secretion possible, and purification thereby easier.

2. Control Sequences and Corresponding Hosts

Procaryotes most frequently are represented by various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar, et al., 1977, *Gene*, 2:95. pBR322 contains genes for ampicillin and tetracycline resistance, and thus provides additional markers which can be either retained or destroyed in constructing the desired vector. Commonly used procaryotic control sequences are defined herein to include promoters for transcription initiation, optionally with an operator, along with ribosome binding site sequences, which include such commonly used promoters as the beta-lactamase (penicillinase) and lactose (aac) promoter systems (Chang, et al., 1977, *Nature*, 198:1056) and the tryptophan (trp) promoter system (Goeddel, et al., 1980, *Nucleic Acids Res.*, 8:4057) and the λ derived $P_L$ promoter and N-gene ribosome binding site (Shimatake, et al., 1981, *Nature*, 292:128), which has been made useful as a portable control cassette, as set forth in U.S. Pat. No. 4,711,845, issued Dec. 8, 1987. However, any available promoter system compatible with procaryotes can be used.

In addition to bacteria, eucaryotic microbes, such as yeast, may also be used as hosts. Laboratory strains of *Saccharomyces cerevisiae*, Baker's yeast, are most used although a number of other strains are commonly available. Examples of plasmid vectors suitable for yeast expression are shown in Broach, J. R., 1983, *Meth. Enz.*, 101:307; Stinchcomb et al., 1979, *Nature*, 282:39; and Tschempe et al., 1980, *Gene*, 10:157 and Clarke, L., et al., 1983, *Meth. Enz.*, 101:300. Control sequences for yeast vectors include promoters for the synthesis of glycolytic enzymes (Hess, et al., 1968, *J. Adv. Enzyme Reg.*, 7:149; Holland, et al., 1978, *Biochemistry*, 17:4900). Additional promoters known in the art include the promoter for 3-phosphoglycerate kinase (Hitzeman, et al. 1980, *J. Biol. Chem.*, 255:2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization (Holland, supra). It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland, M. J. et al., 1981, *J. Biol. Chem.*, 256:1385) or the LEU2 gene obtained from YEp13 (Broach, J. et al., 1978, *Gene*, 8:121), however, any vector containing a yeast compatible promoter, origin of replication and other control sequences is suitable.

It is also, of course, possible to express genes encoding polypeptides in eucaryotic host cell cultures derived from multicellular organisms. See, for example, *Tissue Culture*, 1973, Cruz and Patterson, eds., Academic Press. Useful host cell lines include murine myelomas N51, VERO and HeLa cells, and Chinese hamster ovary (CHO) cells. Expression vectors for such cells ordinarily include promoters and control sequences compatible with mammalian cells such as, for example, the commonly used early and later promoters from Simian Virus 40 (SV40) (Fiers, et al., 1978, *Nature*, 273:113), or other viral promoters such as those derived from polyoma, Adenovirus 2, bovine papilloma virus, or avian sarcoma viruses, or immunoglobulin promoters and heat shock promoters. General aspects of mammalian cell host system transformations have been described by Axel, U.S. Pat. No. 4,399,216, issued Aug. 16, 1983. It now appears also that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes. Plant cells are also now available as hosts, and control sequences compatible with plant cells such as the nopaline synthase promoter and polyadenylation signal sequences (Depicker, A., et al., 1982, *J. Mol. Appl. Gen.*, 1:561) are available. Methods and vectors for transformation of plant cells have been disclosed in PCT Publication No. WO 85/04899, published Nov. 7, 1985.

Host strains useful in cloning and expression herein are as follows:

For cloning and sequencing, and for expression of construction under control of most bacterial promoters, *E. coli* strain MM294 obtained from *E. coli* Genetic Stock Center GCSC #6135. For expression under control of the $P_LN_{RBS}$ promoter, *E. coli* strain K12 MC1000 lambda lysogen, $N_7N_{53}$cI857 SusP80, a strain deposited with the American Type Culture Collection (ATCC 39531), may be used. *E. coli* DG116, which was deposited with the ATCC (ATCC 53606) on Apr. 7, 1987, may also be used.

For M13 phage recombinants, *E. coli* strains susceptible to phage infection, such as *E. coli* K12 strain DG98, can be employed. The DG98 strain has been deposited with the ATCC (ATCC 39768) on Jul. 13, 1984.

Mammalian expression can be accomplished in COS-A2 cells, COS-7, CV-1, hamster and murine cells. Insect cell-based expression can be in *Spodoptera frugiperda*.

3. Transformations

Depending on the host cell used, transformation is done using standard techniques appropriate to such cells. The calcium treatment employing calcium chloride, as described by Cohen, S. N., 1972, *PNAS (USA)*, 69:2110, is used for procaryotes or other cells which contain substantial cell wall barriers. Infection with *Agrobacterium tumefaciens* (Shaw, C. H. et al., 1983, *Gene,* 23:315) is used for certain plant cells. For mammalian cells without such cell walls, the calcium phosphate precipitation method of Graham and van der Eb, 1987, *Virology,* 52:546 is preferred. Transformations into yeast are carried out according to the method of Van Solingen, P. et al., 1977, *J. Bact.*, 130:946 and Hsiao, C. L. et al., 1979, *PNAS (USA)*, 76:3829.

4. Probing mRNA by Northern Blot; Probe of cDNA or Genomic Libraries

RNA is fractionated for Northern blot by agarose slab gel electrophoresis under fully denaturing conditions using formaldehyde, Maniatas, T., et al., 1982, *Molecular Cloning*, Cold Spring Harbor Press, pp. 202–203, or 10 mM methyl mercury ($CH_3HgOH$) (Bailey, J. M., et al., 1976, *Anal. Biochem.,* 70:75–85; Shegal, P. B. et al., 1980, *Nature,* 288:95–97) as the denaturant. For methyl mercury gels, 1.5% gels are prepared by melting agarose in running buffer (100 mM boric acid, 6 mM sodium borate, 10 mM sodium sulfate, 1 mM EDTA, pH 8.2), cooling to 60° C. and adding $\frac{1}{100}$ volume of 1M $CH_3HgOH$. The RNA is dissolved in 0.5×running buffer and denatured by incubation in 10 mM methyl mercury for 10 minutes at room temperature. Glycerol (20%) and bromophenol blue (0.05%) are added for loading the samples. Samples are electrophoresed for 500–600 volt-hr with recirculation of the buffer. After electrophoresis, the gel is washed for 40 minutes in 10 mM 2-mercaptoethanol to detoxify the methyl mercury, and Northern blots prepared by transferring the RNA from the gel to a membrane filter.

cDNA or genomic libraries are screened using the colony or plaque hybridization procedure. Bacterial colonies, or the plaques for phage, are lifted onto duplicate nitrocellulose filter papers (S&S type BA-85). The plaques or colonies are lysed and DNA is fixed to the filter by sequential treatment for 5 minutes with 500 mM NaOH, 1.5M NaCl. The filters are washed twice for 5 minutes each time with 5×standard saline citrate (SSC) and are air dried and baked at 80° C. for 2 hours.

The gels for Northern blot or the duplicate filters for cDNA or genomic screening are prehybridized at 25° to 42° C. for 6 to 8 hours with 10 ml per filter of DNA hybridization buffer without probe (0–50% formamide, 5–6×SSC, pH 7.0, 5×Denhardt's solution (polyvinylpyirolidine, plus Ficoll and bovine serum albumin; 1×=0.02% of each), 20–50 mM sodium phosphate buffer at pH 7.0, 0.2% sodium dodecyl sulfate (SDS), 20 µg/ml poly U (when probing cDNA), and 50 µg/ml denatured salmon sperm DNA). The samples are then hybridized by incubation at the appropriate temperature for about 24–36 hours using the hybridization buffer containing kinased probe (for oligomers). Longer cDNA or genomic fragment probes were labelled by nick translation or by primer extension.

The conditions of both prehybridization and hybridization depend on the stringency desired, and vary, for example, with probe length. Typical conditions for relatively long (e.g., more than 30–50 nucleotide) probes employ a temperature of 42° to 55° C. and hybridization buffer containing about 20%–50% formamide. For the lower stringencies needed for oligomeric probes of about 15 nucleotides, lower temperatures of about 25°–42° C., and lower formamide concentrations (0%–20%) are employed. For longer probes, the filters may be washed, for example, four times for 30 minutes, each time at 40°–55° C. with 2×SSC, 0.2% SDS and 50 mM sodium phosphate buffer at pH 7, then washed twice with 0.2×SSC and 0.2% SDS, air dried, and are autoradiographed at −70° C. for 2 to 3 days. Washing conditions are somewhat less harsh for shorter probes.

5. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 µg of plasmid or DNA sequence is cleaved by 1 unit of enzyme in about 20 µl of buffer solution; in the examples herein, typically, an excess of restriction enzyme is used to insure complete digestion of the DNA substrate. Incubation times of about 1 hour to 2 hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods of Enzymology,* 1980, 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20° to 25° C. in 50 mM dithiothreitol (DTT) and 5–10 µM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease results in hydrolysis of any single-stranded portion.

Synthetic oligonucleotides may be prepared by the triester method of Matteucci et al., 1981, *J. Am. Chem. Soc.,* 103:3185–3191, or using automated synthesis methods. Kinasing of single strands prior to annealing or for labelling is achieved using an excess, e.g., approximately 10 units of polynucleotide kinase to 1 nmole substrate in the presence of 50 mM Tris, pH 7.6, 10 mM MgCl$_2$, 5 mM DTT, 1–2 mM ATP. If kinasing is for labelling of probe, the ATP will contain high specific activity 32YP.

Ligations are performed in 15–30 μl volumes under the following standard conditions and temperatures: 20 mM Tris—Cl pH 7.5, 10 mM MgCl$_2$, 10 mM DTT, 33 μg/ml bovine serum albumin (BSA), 10 mM–50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10–30 fold molar excess of linkers) are performed at 1 μM total ends concentration.

In the vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^{2+}$ and Mg$^{2+}$ using about 1 unit of BAP per μg of vector at 60° C. for about 1 hour. In order to recover the nucleic acid fragments, the preparation is extracted with phenolchloroform and ethanol precipitated. Alternatively, religation can be prevented in vectors which have been double digested by additional restriction enzyme digestion of the unwanted fragments.

6. Modification of DNA Sequences

For portions of vectors derived from cDNA or genomic DNA which require sequence modifications, site specific primer directed mutagenesis is used. This technique is now standard in the art, and is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form: 50% will have the original sequence. The plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

7. Verification of Construction

Correct ligations for plasmid construction could be confirmed by first transforming *E. coli* strain MM294, or other suitable host, with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B. et al., 1969, *PNAS* (*USA*), 62:1159, optionally following chloramphenicol amplification (Clewell, D. B., 1972, *J. Bacteriol,* 110:667). The isolated DNA is analyzed by restriction and/or sequenced by the dideoxy method of Sanger, F., et al. 1977, *PNAS* (*USA*), 74:5463 as further described by Messing et al., 1981, *Nucleic Acids Res.,* 9:309, or by the method of Maxam et al., 1980, *Methods in Enzymology,* 65:499.

E. General Methods of Purifying the Gro β or γ

The general scheme for isolating and purifying the inflammatory cytokines consists of releasing the molecule from the cytoplasm of the appropriate cells, tissues or organs, followed by removing insoluble material and subjecting the soluble fraction to one or more chromatographic steps including anion and cation exchange chromatography. Various purification methods may be used to purify the inflammatory cytokines. Regardless of the procedure chosen, and depending on the nature of the biological material that the inflammatory cytokines are purified from, it may be desirable to have present in the various purification solutions one or more protease inhibitors, for example, PMSF. Additionally, as is known in the art, certain purification steps may be conducted at temperatures that reduce the risk of the inflammatory cytokines being proteolyzed.

More specifically, each inflammatory cytokine is prepared by releasing the molecule from the cytosol using any number of techniques including freeze thawing, sonication, mild detergent extraction, etc. This procedure is preferably carried out in a physiologically buffered solution containing one or more protease inhibitors. Moreover, to further inhibit protease activity, especially those proteases that rely on metal ions for activity, the extraction solution may contain metal ion chelators. The preferred extraction solution is a physiologically balanced salt solution containing the chelators ethyleneglycoltrichloroacetic acid (EGTA), or EDTA, plus the protease inhibitor phenylmethylsulfonylfluoride (PMSF). The metal ion chelator(s), as well as the protease inhibitor(s) are present at concentrations that effectively inhibit proteolysis, preferably about 5 mM and 100 μM, respectively. However, it will, of course, be appreciated by those skilled in the art that since the types and amounts of proteases vary depending on the starting material used to extract the inflammatory cytokine, the concentrations that the protease inhibitors or chelators are used at, if indeed used at all, will also vary.

The mixture containing the inflammatory cytokine is clarified by centrifugation, or in other ways to remove insoluble material from the aqueous cytosol fraction. If the cytosol fraction contains low amounts of the inflammatory cytokine, it can be concentrated by any one of several techniques well known to those skilled in the art, including high salt precipitation, such as, for example, with ammonium sulfate, or by ultra filtration. If the inflammatory cytokine is concentrated by precipitation, it is preferably subsequently resuspended in a suitable physiologically balanced salt solution containing protease inhibitor(s) and which can contain about 0.1% of a nonionic detergent. This solution is then prepared for ion exchange chromatography by dialyzing it against a compatibly buffered chromatographic solution, preferably containing millimolar phosphate, a metal ion chelator, and a protease inhibitor.

The purification procedure would preferably employ at least one ion exchange chromatographic step. An example of a cation exchanger would be SP-cellulose cation exchanger. Such are commercially available from AMF Molecular Separations Division, Meridian, Conn. under the brand name ZetaPrep SP cartridges. The SP-cellulose cation exchanger is an elastic 3-dimensional network composed of cellulosic backbones cross-linked with vinyl polymer containing pendant sulfopropyl functional groups. The matrix is preferably adapted for radial flow passage of the inflammatory cytokine solution. The flow rate of the solution through the matrix will depend upon the size and geometry of the matrix used. It will be apparent to those skilled in the art, however, that care should be taken to avoid exceeding the unit capacity of the matrix with the inflammatory cytokine.

If the capacity is exceeded, the inflammatory cytokine will not be totally retained and excess unretained inhibitor will be present in the effluent. Examples of anion exchange chromatographic materials which can be used are DEAE-Sepharose (Pharmacia Corp.) and TSK-DEAE-5-PW.

As mentioned above, the initial sequence of chromatographic procedures is not rigid, and can be varied. In addition to anion exchange chromatography, other chromatographic methods may be employed, alone or in combination, which are known and practiced in the art. Exemplary methods would include affinity chromatography using, preferably, antibodies specific for the inflammatory cytokines.

The methods for eluting proteins from anion exchangers, and affinity column are well documented and generally known in the art. For example, the inflammatory cytokines can be eluted from DEAE suing a suitably buffered salt gradient, while in the latter instance the addition of a chaotropic agent may be effective. The salt gradient and the concentration of chaotrope can be determined empirically.

A third chromatographic technique that may be used alone or in combination to purify the inflammatory cytokines is by hydrophobic interaction chromatography. A variety of hydrophobic interaction chromatographic matrixes may be utilized. Generally, the materials and methods for utilizing hydrophobic chromatography are described by S. Shaltie, 1984, *Methods in Enzymology*, 104:69. The preparation of such solutions is within the skill of the art.

The purity of the inflammatory cytokines so obtained can be monitored by sodium dodecyl sulfate polyacrylamide gel electrophoresis run under reducing conditions. The general procedures for preparing and using the above purification materials are known to those skilled in the art.

F. General Uses of Gro β and Gro γ

As shown in Example 1 below, the Gro β and γ genes were expressed in the presence of inflammatory agents. Without wishing to be bound by the following postulation, it is postulated that treatments utilizing Gro β and γ would prevent or alleviate the severity of inflammation and the disease or conditions associated therewith.

Example 1 also show that Gro γ was found in colonic epithelial tumor cells but not in adjacent normal epithelial cells. As a comparison, it has been observed that Gro α is over-expressed in other tumor cell lines such as CHEF/16 cells, src-transformed chicken fibroblasts, and human melanomas. On the other hand, it has also been observed that Gro α is expressed in normal growing mammary cells but was absent in many carcinomas. (Anisowicz, A. et al., 1988, *PNAS* (*USA*), supra.) It appears that the differential expression of Gro β or γ in different cell lines may affect the transformation of these cells. Therefore, depending on the cell and tumor types in question, the tumor treatment regimen would involve varying the amount of Gro β or γ accessible to the cells. This can be achieved by either increasing or decreasing the amounts of the Gro proteins available to the cells, depending on whether the tumorigenesis is due to their over- or under- expression of the Gro genes.

Having described what the applicants believe their invention to be, the following examples are presented to illustrate the invention, and are not to be construed as limiting the scope of the invention. For example, variation in: the source of the inflammatory cytokines; the method for inducing, activating and in general producing and obtaining the inflammatory cytokines and antibodies against them; diagnostic tests using them; detection tests for them may be employed without departing from the scope of the present invention.

EXAMPLE 1

A. Procedure

1. Construction and Screening of the Adherent Monocyte cDNA Library for Analogues of Gro The adherent monocyte cDNA library was prepared in the bacterial expression vector λgt10 by using total RNA from human blood monocytes adhered to plastic for 30 minutes at 37° C. The cDNA library used in this application, the construction and screening of the library was performed as described in Sporn, S. A., *J. of Immunol.*, supra. The procedure was as follows.

a) Isolation of Monocytes

Monocytes were isolated from platelet-phoresis residue bags obtained from the American Red Cross (Durham, N.C.). Mononuclear cells were first isolated by Ficoll-Hypaque sedimentation according to the procedure described in Boyum, A., 1986, *Scand. J. Clin. Lab. Invest.*, 21:77 and washed three time with Versene (GIBCO, Grand Island, N.Y.) to remove platelets. Monocytes were then isolated by Percoll density fractionation as described in Ulmer, A. J., et al., 1979, *J. Immunol. Methods,* 30:1 or by adherence to plastic tissue culture dishes (Corning 25020, Corning, N.Y.) as described in Eierman, D. F., et al., 1989, supra.

b) Cell Culture

Monocytes were cultured in endotoxin-free RPMI 1640 (Cell-gro, Fisher Scientific, Raleigh, N.C.) either adherently on plastic at 1 to $2\times10^7$ cells/dish or nonadherently in 50 ml polypropylene tubes (Fisher) at $10^6$ cells/ml (30 ml/tube). Monocytes were cultured serum-free, unless otherwise indicated, at 37° C. in 5% $CO_2$. The coating of plates with fibronectin (FN), collagen, or FN/anti-FN complexes was performed as described in Eierman, D. F., et al., 1989, supra.

c) Construction of a cDNA Library

Total RNA isolated from monocytes adhered to plastic for 30 minutes was used for construction of a cDNA library by using modified methods of Watson and Jackson (Watson, C. J., et al., 1985, in *DNA Cloning*, Vol. 1, *A Practical Approach*, Glover, D. M. ed., IRL Press, Oxford, England, p. 79) and Huynh, T. V. et al., 1985, in *DNA Cloning*, Vol. 1, *A Practical Approach*, Glover, D. M., ed., IRL Press, Oxford, England, p. 49). RNA was converted to dscDNA by using avian myeloblastosis virus reverse transcriptase and the Klenow fragment of DNA polymerase I. dscDNA fragments with EcoR I linkers were size-selected and packaged into λgt10 with the use of Gigapack (Stratagene, San Diego, Calif.). The unamplified library contained approximately $5.3\times10^6$ recombinants at a frequency of $7\times10^7/\mu g$ DNA.

Fifty thousand plaques from the original library were grown and plaque lifts were hybridized to a $^{32}$P-labelled first strand cDNA probes made from time 0 (uninduced) monocyte RNA. In order to reduce the number of clones in the screening that are expressed in uninduced monocytes, 4,000 clones that did not hybridize to the time 0 probe were selected and pooled to form a sub-library. The original library and subsequently the sub-library were hybridized with an IL-1β probe, which is an example of a gene induced by adherence. This demonstrated a 3- to 4-fold enrichment for the induced clones in the sub-library and a depletion of greater than 80% of clones common to adhered and nonadhered monocytes.

d) Screening of the cDNA Library

The sub-library was screened by differential hybridization with $^{32}$P-labelled total first-strand cDNA probes using the procedure described in Huynh, T. V., et al., 1985, supra, prepared from RNA from either 30-minute and 4-hour adhered or nonadhered monocytes. Plaques that preferentially hybridized with the total cDNA probes made from adhered monocytes as opposed to non-adherent monocytes were selected and rescreened. A total of 35 clones out of 111 original isolates remained positive after the second screening.

e) Reagents

PMA, E. coli serotype 055:B5 LPS, the calcium ionophore A23187, and human collagen type I were obtained from Sigma Chemical Co. (St. Louis, Mo.). Human FN and anti-human FN were obtained from Collaborative Research (Bedford, Mass.).

f) Isolation of RNA and Northern Analysis

Total RNA was isolated by using the guanidine isothiocyanate-cesium chloride method as described in Chirgwin, J. M., et al., 1979, Biochemistry, 18:5294. Total RNA (15 µg/lane) was denatured and subjected to electrophoresis on 1% agarose gels containing formaldehyde. RNA was subsequently blotted by Northern transfer (as described in Thomas, P. S., 1980, PNAS (USA), 77:5201) onto nitrocellulose. Clone cDNA inserts were excised from λgt10 vector, $^{32}$P-labelled by nick translation and used as probes for hybridization of Northern blots. The hybridizations were performed at 42° C. as described in Haskill, et al., 1988, supra and blots were washed to a stringency of 0.2×SSC at 56° C.

g) DNA Sequencing cDNA inserts were subcloned into the double stranded vector pGEM blue (Promega Biotec, Madison, Wis.). dsdDNA sequencing was performed by the dideoxy chain termination method (as described in Sanger, F. S., et al., 1977, PNAS (USA), 74:5463) by using the Sequenase sequencing kit (United States Biochemical Co., Cleveland, Ohio) with T7 and SP6 primers (Promega), as well as sequence-specific oligonucleotide primers (Cetus Corp., Emeryville, Calif.).

h) Southern Blot Hybridization

Human monocyte DNA was isolated (as described in Maniatis, T., et al., 1982, Molecular Cloning, Cold Spring Harbor Lab., Cold Spring Harbor, N.Y., p. 382) and digested with the restriction enzymes indicated. The digested DNA was electrophoresed on a 1% agarose gel, denatured, and transferred to nitrocellulose (as described in Southern, E. M., 1975, J. Mol. Biol., 98:503).

B. Result

A 880 bp partial clone (C2m) (designated MAD-2 in Sporn et al., 1990, supra) isolated by subtractive hybridization showed some sequence similarity to the original Gro but contained a number of changes in the 3' coding region. This clone was used to isolate 5 additional clones from a second library produced from mezerin and calcium ionophore stimulated leukocytes, the procedure is described below.

A. Procedure 1. cDNA Library Produced From Mezerein and Calcium Ionophore Stimulated Leukocytes The cDNA was generated from RNA obtained from induced peripheral blood lymphocytes. Such procedures are well known in the art. The preferred procedure consists of inducing peripheral blood cells for three days with a calcium ionophore and mezerein. The preferred ionophore is A-23187. The induction procedure is generally described in U.S. Pat. No. 4,376,821, issued Mar. 15, 1983, "Production of Human IFN-Gamma (Immune) Interferon," to I. A. Braude and U.S. Ser. No. 517,276, filed May 1, 1990 by Haskill et al., "Interleukin-1 Antagonist and Uses Thereof".

More specifically, leukocytes were induced with 100 ng/ml of mezerein and 0.25 µg/ml of calcium ionophore A-23187. The induction period was about 3 days, after which the total RNA was isolated from the induced peripheral blood lymphocytes using essentially the guanidine isothiocyanate-cesium chloride described in Chirgwin et al., 1979, supra, and the poly (A+) messenger RNA were isolated from the total RNA fraction by chromatography on oligo (dT) cellulose as described in Aviv et al., 1972, supra.

Next, the first strand of the cDNA was obtained by reverse transcribing the mRNA as follows. 33 µg of the poly (A+) RNA was dispensed into a micro-centrifuge tube, and incubated for 5 minutes at 65° C., and then cooled on ice for 5 minutes. Next, to the RNA was added sequentially the following: 66 µl of 250 mM Tris—HCl, pH 8.3; 375 mM KCl; 15 mM of MgCl$_2$; 10.0 mM DTT; 9.0 µl RNA's in [40 U/µl]; 16.5 µl of 10 mM dNTP's (i.e., 10 mM dATP+10 mM dCTP+10 mM dGTP+10 mM dTTP); 35.0 µl of p(dT)$_{12-18}$ (100 pmole/µl) (p(dT)$_{12-18}$ denotes oligodeoxythymidilic acid population with lengths of 12 mer, 13 mer, etc., up to 18 mer); and 16.5 µl of murine leukemia virus (MLV)-reverse transcriptase (200 U/µl), and water to bring to a total volume of 330 µl.

To monitor the efficiency of first strand synthesis by alkaline agarose gel electrophoresis, a second tube was prepared that contained 2 µl [α$^{32}$P] dCTP (10 µCi/µl), and 20 µl of the first strand reaction mixture prepared as described above.

Both tubes were incubated for 60 minutes at 37° C. followed by stopping the reactions by putting the tubes on ice. Five µl of 0.5M EDTA and 23 µl of water was added to the tube containing [α$^{32}$P] dCTP. Both tubes were stored at −20° C.

The second strand of the cDNA duplex was prepared as follows. 37.5 µl of the first strand mixture synthesized as described above was aliquoted into 8 separate tubes, on ice. Also, 6.25 µl of the mix was pipetted into a 9th tube, on ice. Next, to each of the 8 tubes, 262.5 µl of a second strand cocktail was added, and to the remaining, or control tube, 43.75 µl was added. The second strand cocktail consisted of the following: 600.0 µl 5×second strand buffer (SSB) (5×SSB consisted of 94 mM Tris—HCl, pH 8.3, 453 mM KCl, 23.3 mM MgCl$_2$, 18.7 mM DTT) 1802.9 µl water, 56.3 µl 10 mM dNTP's, 12.5 µl [α$^{32}$P] dCTP, 75.0 µl mM β-NAD, 75.0 µl DNA polymerase I (10 u/µl), and 3.4 µl of E. coli ligase (9 u/µl). The total volume of the reagents in the second strand cocktail was 2,625.0 µl. All 9 tubes were incubated for 2 hours at 16° C., after which to the 9th tube was added 5 µl of 0.5M EDTA and 65 µl of water. The contents of this tube were stored at −20° C. for subsequent alkaline agarose gel analysis.

Next, the contents of the 8 tubes were phenol extracted and twice ethanol precipitated, and the pellets combined in 128 µl of TE.

The cDNA prepared above was treated with Rnase H as follows. To 128 µl of cDNA was added the following: 128 µl 5×Rnase H buffer which consisted of 100 mM Tris—HCL, pH 7.5, 100 mM KCl, 50 mM MgCl$_2$, 0.7 mM DTT, and 0.5 mM EDTA. Additionally, the tube contained 377.3 µl water, and 6.7 µl of Rnase H (1.9 u/µl). The total volume of the Rnase H reaction digest is 640 µl. The mixture was incubated at 37° C. for 20 minutes after which 5 µl of 0.5M EDTA was added to terminate the reaction. Finally, the reaction mixture was phenol extracted, twice ethanol precipitated, and the pellet resuspended in 12 µl of TE.

The cDNA was fractionated and purified by neutral agarose gel electrophoresis. cDNAs of about 0.25–7.0 kilo bases in length were removed from the gels, glass bead purified, and resuspended in 107.5 µl of glass distilled water.

Next, the cDNA was C-tailed, and cloned into the vector pCDLSRα-296 [obtained from DNAX corporation, and described by Takebe et al., 1988, *Molecular and Cellular Biology*, 8(1):466; and in U.S. Pat. No. 4,695,542 as follows. The 10×terminal deoxynucleotidyl transferase buffer (hereinafter referred to as 10×TdT buffer) was prepared as follows: 13.8 g cacodylic acid was added to 3.0 g Tris-base in 60 ml of water. The solution was adjusted to pH 7.6 by slow addition of solid KOH, after which the volume was increased to 88 ml with water. Subsequently, the solution was chilled to 0° C., then 2 ml of 0.1M DTT was added followed by the addition of 10 ml of 0.1M $MnCl_2$ dropwise while the solution was being constantly stirred. To the 38.3 $\mu$l of 10×TdT buffer was added 5.7 $\mu$l of 1 mM dCTP, and 0.6 $\mu$g of double stranded cDNA. An amount of water was added to bring the solution to a total volume of 380.5 $\mu$l. The solution was warmed to 37° C. for 15 minutes, and 360 units of TdT in about 3 $\mu$l was added. 60 $\mu$l aliquot was removed at various times and combined with 468 $\mu$l of 1 mM EDTA. Each aliquot was then combined with previously G-tailed vector in a suitable amount of annealing buffer, and transformed into an appropriate host. The C-tailed stock that produced the greatest number of transformants was used for the large scale transformation.

The cDNAs were cloned into the plasmid vector, pCDL-SRα296. The vector was prepared as follows. 200 $\mu$g of the plasmid was digested with 700 units PstI in 500 $\mu$l total volume, for 60 minutes at 37° C. The plasmid was then phenol extracted, and twice ethanol precipitated, and resuspended in 200 $\mu$l of distilled water. The concentration was determined by spectrophotometry. Next, about 136 $\mu$g of pCDL-SRα296, 112.6 pmole 3' ends, was G-tailed by combining it in a solution consisting of 30 $\mu$l of 10×TdT buffer, 30 $\mu$l [$^3$H] dGTP (approximately 70 pmole/$\mu$l), 5.5 $\mu$l of 1 mM dGTP and water to make a total volume of 297 $\mu$l. The tailing reaction was conducted for various times, and the procedure consisted of removing 30 $\mu$l from the reaction tube and combining it with 359 $\mu$l of 17 mM EDTA, which was the 0 time point. Next, 360 units of terminal transferase in 3 $\mu$l was added to prewarmed reaction digest mixture, 15 minutes at 37° C., and 30 $\mu$l of the mixture removed at various time intervals and the reactions stopped by pipetting it into 359 $\mu$l of 17 mM EDTA. The amount of G-tailing was monitored by determining the incorporation of [$^3$H] dGTP, as is known in the art. To ensure that the pCDL-SRα296 vector was properly G-tailed and that it was not contaminated with untailed vector, a trial annealing and transformation of DH5α bacteria was conducted as is known in the art. (DH5X bacteria was obtained from Bethesda Research Laboratories, Research Products Division, Life Technologies, Inc., Gaithersburg, Md. 20877. Cat. No. 82585A: Max Efficiency DH5α™ competent cells.) The vector was stored at –20° C. and used to clone the above described C-tailed cDNA.

Briefly, cloning into pCDL-SRα296 consisted of combining 88 $\mu$l of C-tailed cDNA corresponding to each time point, 2 $\mu$l G-tailed vector, and 10 $\mu$l of 10×annealing buffer. The total volume was 100 $\mu$l. The 10×annealing buffer consisted of: 0.1M Tris—HCL, pH 7.6, 1.0M NaCl, 10 mM EDTA. The annealing reaction was conducted under standard conditions, and the mixture transformed into DH5 bacteria.

The cDNA library obtained above may be amplified using either procedures well known in the art, or a novel solid state amplification technique described as follows. The procedure consisted of suspending bacterial transformants in low melting temperature agarose. This is contrary to the state of the art methods that plate the bacterial transformants on suitable culture dishes. The following materials and methods were utilized. 0.3% Seaprep agarose in 2×LB media (2% bactotryptone, 1% yeast extract, 1% NaCl, pH 6.9. The bactotryptone and yeast extract were obtained from Difco Laboratories, Inc., Detroit, Mich.), maintained at 37° C. in a water bath. An appropriate amount of cDNA annealed to pCDL-SRα296 and transformed into DH5α bacteria to generate up to about $2.5 \times 10^6$ cfu/ml. To the appropriate amount of agarose was added ampicillin to make 50 $\mu$g/ml and approximately $1.25 \times 10^6$ cfu of bacterial transformants. 25 ml of this solution was poured into 50 ml conical tubes (Falcon Corp. No. 2098). The tubes were placed in an ice water bath for 20–60 minutes, and incubated overnight at 37° C. To assess the titre of the transformant mixture, 100 $\mu$l was plated on LB-amp$^{50}$ (amp$^{50}$ denotes 50 $\mu$g/ml ampicillin) plates.

The library may be stored by pelleting the cells in 500 ml centrifuge bottles at 8K for 20 minutes at room temperature. The cell pellets were resuspended in a total volume of 100 ml of 12.5% glycerol in LB media. Aliquots of the suspension were stored at –70° C.

2. Origin and Culture of Cells

Monocytes and lymphocytes were isolated from normal blood by Ficoll-Hypaque and subsequent Percoll density separation as described previously (Eierman, D. F., et al., 1989, supra). Neutrophils were purified by sedimentation of the Ficoll-Hypaque pellet in a 3% gelatin/PBS (phosphate buffered saline solution without Ca++ and Mg++) for 1 hour at 37° C. Monocytes, lymphocytes and neutrophils were cultured in serum-free RPMI medium (GIBCO, Grand Island, N.Y.) on plastic dishes which had previously been coated with fibronectin, or on plastic with 1 $\mu$g/ml bacterial endotoxin lipopoly-saccharide (LPS) or were cultured under non-adherent conditions with 5 ng/ml of a known tumor promoter phorbol 12-myristate 13-acetate (PMA) (Eierman, D. F., et al., 1989, supra). Second passage human umbilical vein endothelial cells (HUVE) were cultured in 10% fetal calf serum in RPMI medium for 4 hours with 5 $\mu$g/ml LPS. Colon carcinoma cells were derived from a fresh surgical specimen. Diagnosis was confirmed by histology.

3. Isolation of Genomic Clones

Approximately $8 \times 10^5$ plaques of a human female leukocyte library in λ EMBL 3 were screened with $^{32}$P labelled Gro α cDNA probe. Positive clones were subcloned into pGEM3 or pGEM4Z plasmids and the whole plasmid or ExoIII nested deletion plasmids were sequenced by the dideoxy chain termination method. The three Gro gene clones were distinguished by restriction fragment analysis.

4. Analysis of RNA and DNA

RNA analysis was carried out by PCR. For PCR, 1 $\mu$g of total RNA was converted into first strand cDNA with random hexamers as described by Kawasaki, E. S., et al., 1990, *PCR Technology*, (Erlich, H. A., ed.) Stockton Press, New York, pp. 89–97. Amplification was carried out using a sense primer that was common to the different Gro clones and anti-sense primers specific for each. Gro α was detected with GM135 and GM350; Gro β with ML80 and GM272; and Gro γ with GM135 and GM221 (see FIGS. 1(a) and (b)).

Amplifications were carried out to 25, 30 and 35 cycles to verify that reactions were proceeding exponentially. Data shown is from 30 cycles at which time all samples had not yet reached maximum intensity. Southern transfer analysis was carried out following transfer to nitrocellulose for random primed cDNA probes or by direct oligonucleotide hybridization to dehydrated agarose gels as described in Southern, E. M, 1975, supra and Siebert, P. D., et al., 1989, *Clontech Laboratories* 1989 *Technical Report,* 6–9. Washing was carried out to a final stringency of 2×SSPE (2×SSPE consisted of 0.3M NaCl, 0.02M NaH$_2$PO$_4$, and 0.002M EDTA) at 56° C. for oligonucleotides and 0.2×SSC, at 65° C. for cDNA probes.

B. Results

1. Characterization of Two Novel Gro Gene cDNAs

During isolation of cDNAs by substrative hybridization from adherent vs. nonadherent monocytes (described in Sporn, S. A., et al., 1990, supra), partial clone with a Gro-related sequence was identified, and using this sequence as probe against the leukocyte cDNA library above, full length versions of two sequences, designated Gro β and Gro γ were recovered.

In summary, one of the 5 clones, isolated from the above mezerin and calcium ionophore stimulated leukocyte cDNA library, was designated Gro β. Gro β contained a PstI and NcoI restriction pattern similar to the C2m isolate. Primers GM135, GM221, GM297, GM298, GM316, GM349, GM350 and ML80 (shown in FIGS. 1(a) and (b)) were constructed which permitted bi-directional sequencing of the double strand templates. In the case of Gro β, a partial clone (C2m) (Designated MAD-2 in Sporn, S. A., et al, 1990, J. of Immunol., supra), a full-length clone containing 2 introns (CC2b) and polymerase chain reaction (PCR) product were used to confirm the complete cDNA sequence.

A partial description of the Gro β gene is inferred from sequencing of CC2b. The result showed close nucleic acid homology between CC2b and Gro α and Gro γ at the 5' end up to the start of the mature protein. Thereafter, 95 nucleic acids intervened before the homology began again over the first 41 amino acids of the mature protein. Then another insertion of 118 nucleic acids intervened before the homology began again for another 84 amino acids. Without wishing to be bound by the following postulation, we postulate that the 95 and 118 nucleic acid fragments without homology to Gro α and Gro γ cDNAs represent introns of the Gro β gene, and that this particular cDNA, CC2b, represents a failure of the cell to completely process out the introns.

Another clone (Gro γ) was represented 3 times in this screening. The remaining isolate appeared to have PstI and NcoI restriction characteristics of the original Gro clone Gro α. All three different (i.e., Gro α, β and γ) clones were sequenced and their cDNA sequences are shown in FIGS. 1(a) and (b).

Sequence comparisons of the α, β and γ forms are also given in FIGS. 1(a) and (b). Gro β and Gro γ share 93% and 82% identity, respectively, with Gro α at the nucleotide level. Compared with Gro α, there are 11 amino acid substitutions in Gro β, 8 resulting from first and/or second position changes. Of the 11, 9 are located in the secreted peptide beyond the signal peptide cleavage point.

Compared with Gro α sequence, there are 15 amino acid changes in Gro γ, 11 of which are in the secreted peptide region. In addition, there is a codon deletion in Gro γ at bp157.

In the 3' untranslated region, Gro β has 11 ATTTA repeats, 6 of them in a single stretch at bp543. In contrast, Gro α and Gro γ contain 5 and 6 repeats, respectively. In addition, a 64 bp region and a 58 bp region 3' to it are highly conserved among the 3 Gro variants (beginning at bp847, 870 and 852, in Gro α, β and γ respectively). The intervening 25 bp are conserved in Gro α and β. The 3'58 bp of the region (930–987) are also conserved in the hamster gene, as previously shown (Anisowicz, A., et al., 1987, supra).

2. DNA Hybridization Analysis Identifies Three Gro Genes

Southern blot hybridization with Gro α, β, and γ cDNA probes gave similar restriction fragment patterns with the enzymes XbaI and EcoRI, as well as extra bands characteristic of each cDNA. In FIG. 2, these patterns (lanes 1, 2 and 3) were compared with Southern blots using oligonucleotide probes common to the three cDNAs (lanes 4 and 5) as well as Gro α-specific (lane 6) and β-specific (lane 7) probes. In the EcoRI digests, the common probe ML80 identified three bands at 6.6, 4.4 and 3.3 kb. (The sequence for ML80 is as shown in FIG. 1(b).) With the Gro α-specific probe GM350, only the 4.4 kb band was seen (lane 6); and with the β-specific probe GM272 only the 3.3 kb band was seen. ML80 also detected the 6.6 kb γ-specific DNA seen only in lane 3. Similarly in the XbaI digests the results are consistent in identifying three genes.

Figure 3:
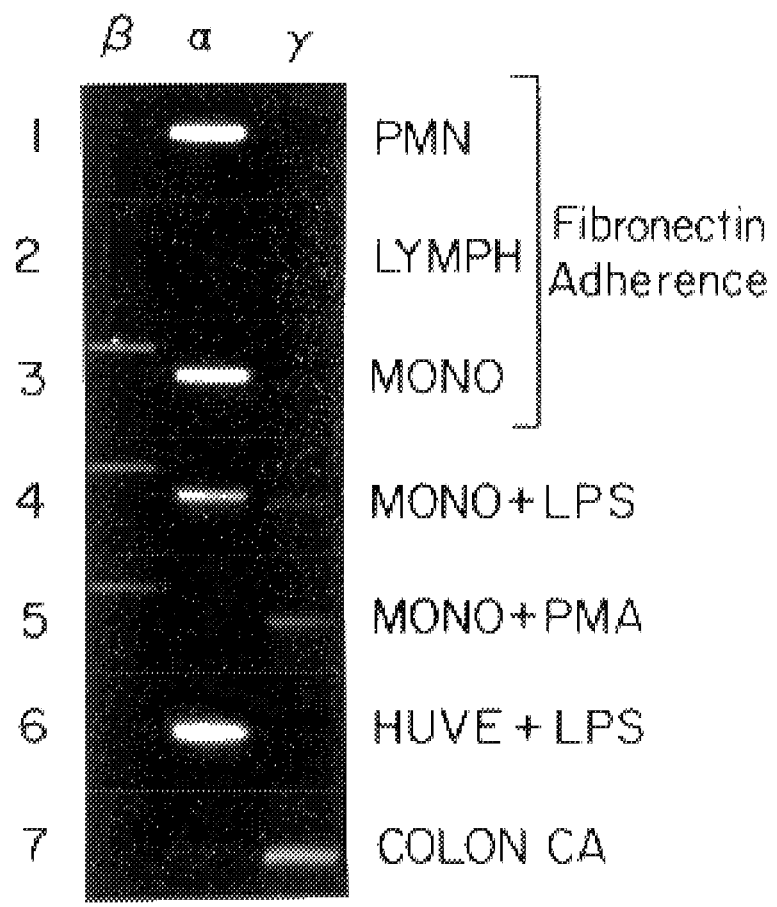
FIG. 3 shows the PCR analysis of Gro expression in different cells from the same individual or similar cells from different individuals stimulated by different signals. Lane 1, neutrophils; 2, lymphocytes; and 3, monocytes, each adhered for 45 minutes to fibronectin coated plastic; 4, adherent monocytes stimulated with bacterial polysaccharide (LPS) for 4 hours; 5, monocytes stimulated under non-adherent conditions with phorbol 12-myristate 13-acetate (PMA) for 4 hours; 6, endothelial cells stimulated with LPS; and 7, fresh biopsy of colonic carcinoma. All data are shown at 30 amplification cycles.

3. Expression of the Three Gro Genes is Differentially Regulated in a Tissue and Signal Specific Manner Utilizing PCR primer pairs specific for each of the 3 Gro cDNAs, the expression of these genes was characterized in (1) inflammatory cells from a single donor (neutrophils, lymphocytes and monocytes); (2) umbilical vein endothelial cells; and (3) a freshly isolated colon carcinoma from a different donor (FIG. 3). Neutrophils which adhered to fibronectin produced only the Gro α version. Lymphocytes produced Gro α only, whereas monocytes expressed all three Gro molecules. Thus, different cells from the same donor stimulated by adherence to the same extracellular matrix component showed selective Gro gene expression.

However, in the same cell type, different inducers stimulated different patterns of Gro expression. Non-adhered monocytes stimulated with PMA expressed only the Gro β and Gro γ forms while monocytes treated with LPS expressed all 3 versions. Human umbilical vein endothelial cells stimulated with LPS expressed only the Gro α gene product. Expression of the Gro γ gene was not restricted to macrophages; freshly isolated and dissected colonic epithelial tumor cells were found to express predominantly the Gro γ version by PCR analysis. In the same study, the normal colonic epithelial cells adjacent to the tumor cells did not express detectable level of Gro γ.

These results confirm that all three forms of Gro are expressed in the induced cells. However, the results do not provide a precise quantitative comparison, since the relative hybridization constants for the three probes may differ.

EXAMPLE 2

Methods for Identifying or Detecting Inflammatory and Anti-Inflammatory Agents

A. Procedure

1. Methods for Identifying or Detecting Inflammatory Agents

As Example 1 indicates, the monocytes under the following conditions expressed Gro β or γ: 1) monocytes which adhered to fibronectin; 2) non-adhered monocytes stimulated with PMA; and 3) non-adhered monocytes treated with LPS. Since PMA stimulates Gro β and γ expression in non-adhered monocytes, this indicates that the expression of these Gro genes were due to the presence of inflammatory agents, such as PMA and LPS.

Thus, an assay system may be established for screening potential chemicals that may modulate the synthesis, release, or activity of the inflammatory cytokines. More particularly, the assay could be used to determine if a chemical X could be an inflammatory agent. By varying the concentration of X and assaying the levels of expression of Gro β and γ, it could also be determined at what concentration X would trigger an inflammatory response, and the potential severity of the inflammatory response at different concentrations. For example, a sample of monocytes could be exposed to X in various amounts, preferably under nonadherent conditions, for an appropriate period of time to allow for the expression of the Gro β or γ gene. Then the RNAs from the monocytes are collected and probed with DNA probes for Gro β and γ, using the hybridization or PCR procedures described under the Procedure section of Example 1(A)(4). In situ hybridization could also be used using methods known in the art. The procedures for obtaining, culturing and incubating the monocytes with X would be similar to those set forth under the Procedure section of Example 1, for monocytes exposed to LPS on PMN. One skilled in the art would be able to appropriately modify the procedures and the incubation time for the particular X used. This test would be useful if X has been proposed as a potential drug, as it would alert the potential users of its inflammatory effect and the proper precautions to be taken.

Alternatively, the Gro β and γ could be detected using the immunological procedures generally described supra.

2. Methods for Identifying or Detecting Anti-Inflammatory Agents

The methods shown above could be modified to identify or detect anti-inflammatory agents. Thus, an assay system may be established for screening potential chemicals that may modulate the synthesis, release, or activity of the inflammatory cytokines. More particularly, the assay could be used to determine if a chemical Y could be an anti-inflammatory agent. The procedure would involve exposing a sample of monocytes to a known inflammatory agent, such as PMS or LPS, for a sufficient time for the expression of Gro β or γ. Then Y is added to the culture. After an appropriate period of incubation, the RNAs from the monocytes are collected and purified and probed with DNA probes for Gro β or γ, using the procedure described under the Procedure section of Example 1(A)(4). In situ hybridization could also be used. Alternatively, the Gro β and γ protein could be detected using the immunological procedures generally described supra. By varying the concentration of Y and assaying the levels of expression of Gro β and γ, it could also be determined at what concentration Y is effective as an anti-inflammatory agent.

The procedures for obtaining, culturing and incubating the monocytes with X would be similar to those set forth under the "Procedure" section of Example 1, for monocytes exposed to LPS on PMN. One skilled in the art would be able to appropriately modify the procedures for the particular Y used and the appropriate incubation times for the inflammatory and potential anti-inflammatory agents. The methods are useful in identifying anti-inflammatory agents and finding novel anti-inflammatory agents. The methods can also be used to determine the efficacy of and the appropriate dose levels for novel or known anti-inflammatory agents.

EXAMPLE 3

Diagnostic for Colonic Epithelial Tumor Cells

As shown in Example 1, Gro γ was found in colonic epithelial tumor cells but not in adjacent normal epithelial cells. Therefore, colonic epithelial tumor could be diagnosed by assaying for the differential expression of Gro γ gene in the colonic epithelial cells. A preferred assay procedure would involve the hybridization of mRNA, collected from the epithelial cells to be tested, to a DNA probe for Gro γ. In situ hybridization could also be used. The preferred procedure is the hybridization or PCR procedure described under the Procedure section of Example 1(A)(4). The preferred DNA probe would be GM221.

EXAMPLE 4

Synthesis of Peptide Sequences

The peptides containing the sequences of Gro β and γ may be synthesized by methods well known in the art. The preferred method of peptide synthesis is the solid-phase method, described in more detail in Metrifield, R. B., 1985, Science, 232:341–347, on a Biosearch 9500 automated peptide machine, cleaved with hydrogen fluoride and purified by preparative HPLC using a Waters Delta Prep 3000 instrument, on a 15–20 μm Vydac CH Prep PAK column. An alternative method is by means of ABI Automatic Synthesis. These synthetic peptides can be used to raise the polyclonal and monoclonal antibodies to Gro β and γ (see Example 5 below).

EXAMPLE 5

Production of Antibodies to Gro β and γ

Antibodies to the inflammatory cytokines are produced using standard procedures known in the art. For example, antibodies are produced by injecting a host animal such as rabbit, rat, goat, mouse, etc., with the Gro β and γ proteins, or peptide fragments thereof, alone or conjugated to an appropriate carrier if required to elicit an antibody response. Examples of the preferred peptides for raising antibodies against these Gro proteins are:

Cys-$(Gly)_{1-3}$-5'-Asn;

Cys-$(Gly)_{1-3}$-5'-Gly; and

Cys-$(Gly)_{1-3}$-5'-$(Gly)_{1-3}$-5'-Gly.

For Gro β, the 5' mer would be: Lys-Asn-Gly-Lys-Ser. For Gro γ, the 5' mer would be: Lys-Lys-Gly-Ser-Thr. The term $(Gly)_{1-3}$ denotes one to three glycine residues.

Further, Gro β and γ, or peptide fragments can be combined with an adjuvant, for example, complete Freund's adjuvant, and used to immunize the host animals. Alternatively, before injection into the host animals, these proteins or peptides may be conjugated with keyhole limpet hemocyanin (KLH) or bovine serum albumin (BSA). The conjugation is achieved via the sulfhydryl group in the cysteine residue. The methods for such conjugation and the production of antibodies using the conjugate thus produced are described in U.S. Pat. No. 4,762,706, issued Aug. 9, 1988, to McCormick et al. It will be appreciated by those skilled in the art that monoclonal antibodies (MABs) to the above Gro β and γ are produced by means of the hybridoma technique. These monoclonal antibodies are useful for assaying the Gro proteins in an immunoassay as shown above.

The present invention has been described with reference to specific embodiments. However, this application is intended to cover those changes and substitutions which may be made by those skilled in the art without departing from the spirit and the scope of the appended claims.

We claim:

1. A method for determining whether a chemical has inflammatory activity, comprising the steps of: measuring Gro β or γ level in inflammatory responsive cells which have been exposed to the chemical, and comparing the Gro β or γ level to that of cells which have not been exposed to the chemical.

* * * * *